(12) United States Patent
Taylor et al.

(10) Patent No.: US 9,089,885 B2
(45) Date of Patent: Jul. 28, 2015

(54) PATIENT ROOM CLEANING SYSTEM AND METHOD

(75) Inventors: Raymond J. Taylor, Hamilton, MA (US); Graeme Crothall, Gladwyne, PA (US)

(73) Assignee: Xanitos, Inc., Radnor, PA (US)

( * ) Notice: Subject to any disclaimer, the term of this patent is extended or adjusted under 35 U.S.C. 154(b) by 228 days.

(21) Appl. No.: 13/154,290

(22) Filed: Jun. 6, 2011

(65) Prior Publication Data

US 2011/0284026 A1 Nov. 24, 2011

Related U.S. Application Data

(63) Continuation-in-part of application No. 11/457,627, filed on Jul. 14, 2006, now abandoned.

(60) Provisional application No. 60/699,961, filed on Jul. 15, 2005.

(51) Int. Cl.
*G06Q 10/00* (2012.01)
*B08B 13/00* (2006.01)
*A47L 5/36* (2006.01)
*A47L 9/00* (2006.01)
*A47L 13/51* (2006.01)
*A61L 2/18* (2006.01)
*G06Q 10/06* (2012.01)

(52) U.S. Cl.
CPC . *B08B 13/00* (2013.01); *A47L 5/36* (2013.01); *A47L 9/009* (2013.01); *A47L 9/0018* (2013.01); *A47L 13/51* (2013.01); *A61L 2/18* (2013.01); *G06Q 10/06311* (2013.01)

(58) Field of Classification Search
USPC .............................................. 705/7.11–7.42
See application file for complete search history.

(56) References Cited

U.S. PATENT DOCUMENTS

| 3,651,536 A | | 3/1972 | Bolzan et al. |
| 3,869,265 A | | 3/1975 | Wolter et al. |
| 4,019,027 A | * | 4/1977 | Kelley ........................ 235/89 R |
| 4,739,535 A | | 4/1988 | Schuld et al. |
| 4,810,269 A | * | 3/1989 | Stackhouse et al. ............ 96/381 |
| 5,089,037 A | | 2/1992 | Marsolais |
| 5,111,391 A | * | 5/1992 | Fields et al. ...................... 705/9 |

(Continued)

OTHER PUBLICATIONS http://www.etcpads.com/BOOK2.HTML (retrieved from Internet Archive, Mar. 6, 2001).*

(Continued)

*Primary Examiner* — Alan S Miller
(74) *Attorney, Agent, or Firm* — Baker & Hostetler LLP

(57) ABSTRACT

A method improving air quality and reducing healthcare-associated infections performed by a cleaning personnel includes the steps of equipping a cleaning cart with a plurality of single-use microfiber cloths and a plurality of microfiber mops, wherein the cleaning cart includes a vacuum cleaning apparatus with an extensible vacuum hose and a plurality of attachments, positioning the cleaning cart outside of an occupied patient room, vacuuming the patient room with the vacuum hose including first and second attachments, disinfecting the surfaces that a patient may contact with a first microfiber cloth soaked in a disinfectant solution, cleaning at least one bathroom fixture with a second microfiber cloth soaked in the disinfectant solution, mopping the floor area including the floor area of the patient restroom with a microfiber mop charged with a neutral cleaner, and placing the microfiber mop in a plastic bag.

9 Claims, 15 Drawing Sheets

(56) References Cited

U.S. PATENT DOCUMENTS

| | | | |
|---|---|---|---|
| 5,155,876 A | 10/1992 | Whitaker | |
| 5,851,117 A * | 12/1998 | Alsheimer et al. | 434/219 |
| 5,890,134 A * | 3/1999 | Fox | 705/9 |
| 5,911,134 A * | 6/1999 | Castonguay et al. | 705/9 |
| 5,943,652 A * | 8/1999 | Sisley et al. | 705/9 |
| 6,047,297 A * | 4/2000 | Johnson et al. | 715/210 |
| 6,216,108 B1 * | 4/2001 | LeVander | 705/7 |
| 6,308,163 B1 * | 10/2001 | Du et al. | 705/8 |
| 6,390,822 B1 * | 5/2002 | Murphy et al. | 434/219 |
| 6,418,361 B2 * | 7/2002 | Sinex | 701/29 |
| 6,678,714 B1 * | 1/2004 | Olapurath et al. | 718/104 |
| 6,691,006 B2 * | 2/2004 | Sinex | 701/29 |
| 6,714,913 B2 * | 3/2004 | Brandt et al. | 705/2 |
| 6,804,857 B1 | 10/2004 | Olewiler | |
| 7,003,475 B1 * | 2/2006 | Friedland et al. | 705/9 |
| 7,340,679 B2 * | 3/2008 | Botscheck et al. | 715/738 |
| 2001/0053939 A1 * | 12/2001 | Crevel et al. | 700/9 |
| 2002/0082883 A1 * | 6/2002 | Hankinson | 705/7 |
| 2004/0019513 A1 * | 1/2004 | Colalancia et al. | 705/9 |
| 2005/0027589 A1 * | 2/2005 | Jenkins et al. | 705/11 |
| 2005/0081898 A1 | 4/2005 | Williams et al. | |
| 2007/0067199 A1 * | 3/2007 | Shine et al. | 705/9 |
| 2009/0193973 A1 | 8/2009 | Woods | |

OTHER PUBLICATIONS

Custodial Solutions 8 (Custodial Solutions 8 Fact Sheet by Breeze Software, http://web.archive.org/web/20020802053025/breeze-software.com/Cleanfacts.htm.*
James P Connors (Using work teams and high efficiency vacuums to clean patient rooms; Healthcare Purchasing News; Mar. 2005; 29, 3; ABI/INFORM Trade & Industry p. 34).*
Health Care Seminar (retrieved from http://wayback.archive.org/web/*/http://www.huskybrand.com/documents/pdfs/* Sep. 2004).*
Guidelines for Environmental Infection Control in Health Care Facilities (Recommendations of CDC and Healthcare Infection Control Practices Advisory Committe (HIPAC), U.S. Department of Health and Human Services, Centers Fro Disease Control and Prevention (CDC), 2003.*
Breeze Software; Custodial Solutions 8; http://web.archive.org/web/20020802053025/breezesoftware.com/Cleanfacts.htm.
Article; Self-Study: Using work teams and high efficiency vacuums to clean patient rooms. By: James P. Connors, CHESP Mar. 2005; Healthcare purchasing; www.hponline.com.
Schmidt et al, "Improved System for Floor Cleaning in Health Care Facilities" Applied and Environmental Microbiology, May 1984, 47(5):942-946.

* cited by examiner

PATIENT ROOM CLEANING SYSTEM AND METHOD

RELATED APPLICATION

This application is a continuation-in-part of and claims priority benefit to U.S. patent application Ser. No. 11/457,627, titled "LOW PATIENT ROOM CLEANING SYSTEM AND METHOD", filed on Jul. 14, 2006, which claims the benefit of priority to U.S. Provisional Patent Application Ser. No. 60/699,691, filed Jul. 15, 2005, each of which is hereby incorporated by reference in its entirety into the present application.

BACKGROUND OF THE INVENTION

1. Field of the Invention

The present invention relates to cleaning methods. More particularly, the invention relates to a method of improving air quality and reducing healthcare-associated infections utilizing a cleaning cart with a vacuum cleaning apparatus.

2. Description of the Related Art

Traditional methods for cleaning a patient's area in a medical facility include dry mopping and dusting. Such methods can disperse dust particulates throughout the patient's environment, decreasing air quality. The dust particulates also resettle and contaminate surfaces thought to be clean. Airborne dust could also be breathed by the patient, leading to infections and lowering health quality. Traditional cleaning methods have also included mopping floors using a bucket that is moved from room to room without changing or refreshing the cleaning solution. This approach can lead to cross contamination of bacteria from one room to the next.

SUMMARY OF THE INVENTION

The present invention solves the above-described problems and provides a distinct advance in the art of cleaning methods. More particularly, the invention provides a cleaning method that utilizes a cleaning cart equipped with a vacuum cleaning apparatus. In addition, cleanliness is improved and contamination is reduced by the single-use techniques of the invention.

The present invention offers improvements over traditional cleaning practices in that a team of members is employed with specific tasks to focus on areas in which patients are residing. Each member is assigned a specific job to perform in a given area and the members rotate job assignments on a regular schedule. As opposed to traditional cleaning techniques that allow dust particulates to become airborne, some embodiments of the present invention utilize damp cleaning with single-use disinfected cloths to clean a patient area, leading to an improvement in air quality and a reduction in the risk of illnesses associated with airborne pollutants and infectious matter. Some embodiments of the present invention also use microfiber, disinfected mops that are discarded after one use to clean all floor areas, resulting in a reduction in the risk of cross contamination.

For example, in one embodiment, the present invention provides a method of cleaning a patient area having a floor area. The method generally includes creating a team including a plurality of team members. A first and a second team member are assigned to remove trash from the patient area. The first and second team members are assigned to scan the floor area for large debris and remove the debris. A third team member is assigned to vacuum the floor area. The first team member is assigned to damp clean the patient area. The second team member is assigned to mop the floor area.

In another embodiment, the method generally includes creating a three-member team, comprising first, second, and third team members. The first and second team members are assigned to remove trash from a patient area. The first and second team members are assigned to scan a floor area for large debris and remove the debris. The third team member is assigned to vacuum the floor area. The first team member is assigned to damp clean the patient area. The second team member is assigned to damp clean the floor area with a microfiber mop.

In another embodiment, the method includes creating a three-member team, comprising first, second, and third team members. The first and second team members are assigned to remove trash from a patient area and deposit the trash in a mobile trash apparatus. The first and second team members are assigned to scan a floor area for large debris and remove the debris. The third team member is assigned to vacuum the floor area using a vacuum cart with a HEPA-filtered vacuum. The first team member is assigned to damp clean the patient area utilizing single-use cloths that are soaked in a disinfectant solution and discarded after one use. The second team member is assigned to damp clean the floor area with a microfiber mop that is soaked in a disinfectant solution and discarded after one use. After a period of approximately thirty minutes, the various assigned tasks are rotated.

One embodiment of the present invention is a method of improving air quality and reducing healthcare-associated infections performed by a cleaning personnel in a patient area including a patient room, a patient restroom, and a floor area that includes the steps of: equipping a cleaning cart with a plurality of single-use microfiber cloths and a plurality of microfiber mops, wherein the cleaning cart includes a vacuum cleaning apparatus with an extensible vacuum hose and a plurality of attachments; positioning the cleaning cart outside of an occupied patient room; putting a first pair of gloves on the hands of the cleaning personnel; extending the vacuum hose into the patient room; vacuuming the above-floor surfaces with a first attachment; vacuuming the floor area with a second attachment; dipping the first attachment in a bucket filled with a first disinfectant solution; disinfecting the surfaces that a patient may contact with a first microfiber cloth soaked in a second disinfectant solution; cleaning at least one bathroom fixture with a second microfiber cloth soaked in the second disinfectant solution; removing the first pair of gloves from the hands of the cleaning personnel; washing the hands of the cleaning personnel; putting a second pair of gloves on the hands of the cleaning personnel; mopping the floor area including the floor area of the patient restroom with a microfiber mop charged with a neutral cleaner; and placing the microfiber mop in a plastic bag.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

Figure 1:
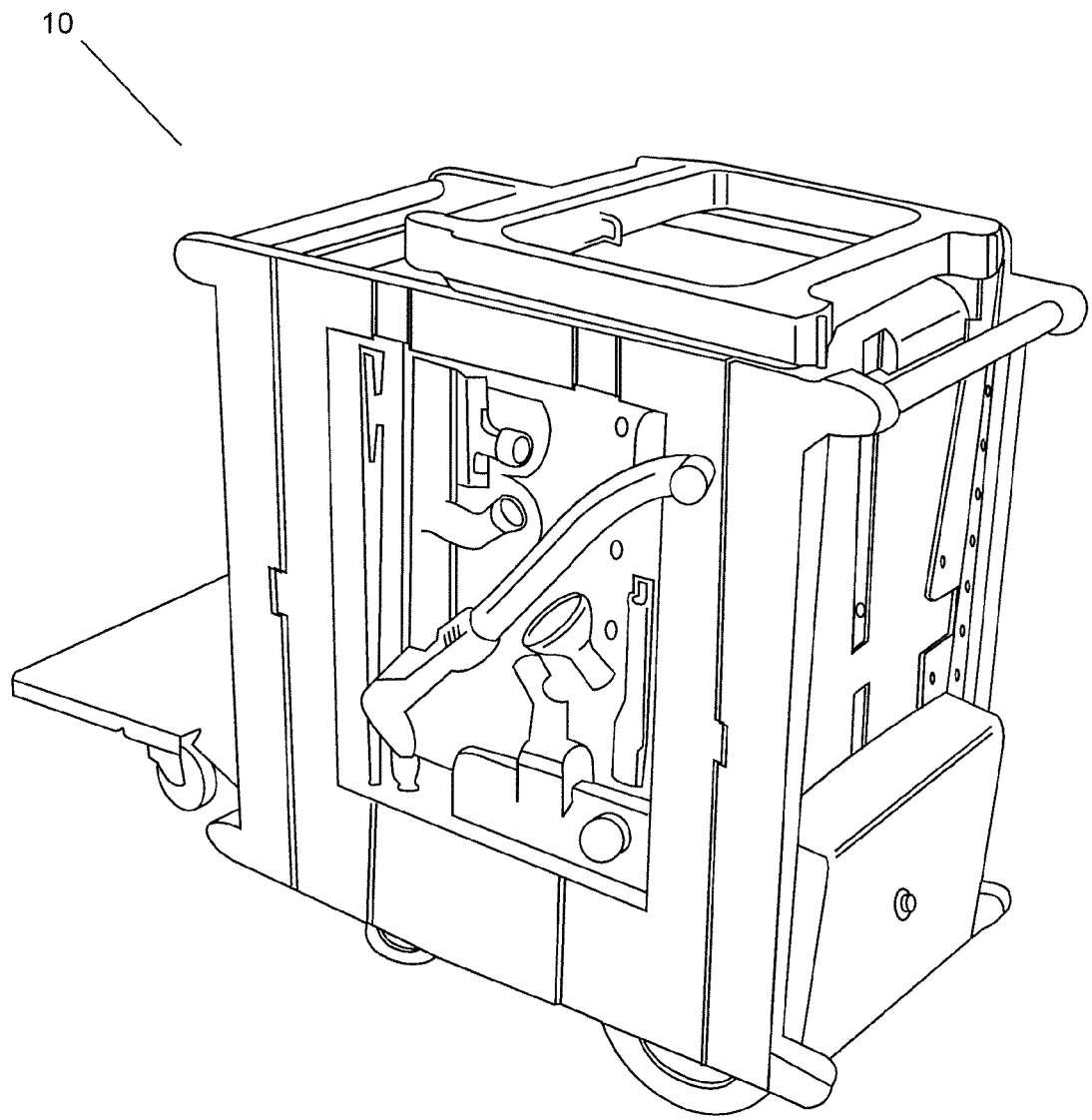
FIG. 1 is a rear perspective view of a cleaning cart.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 2:
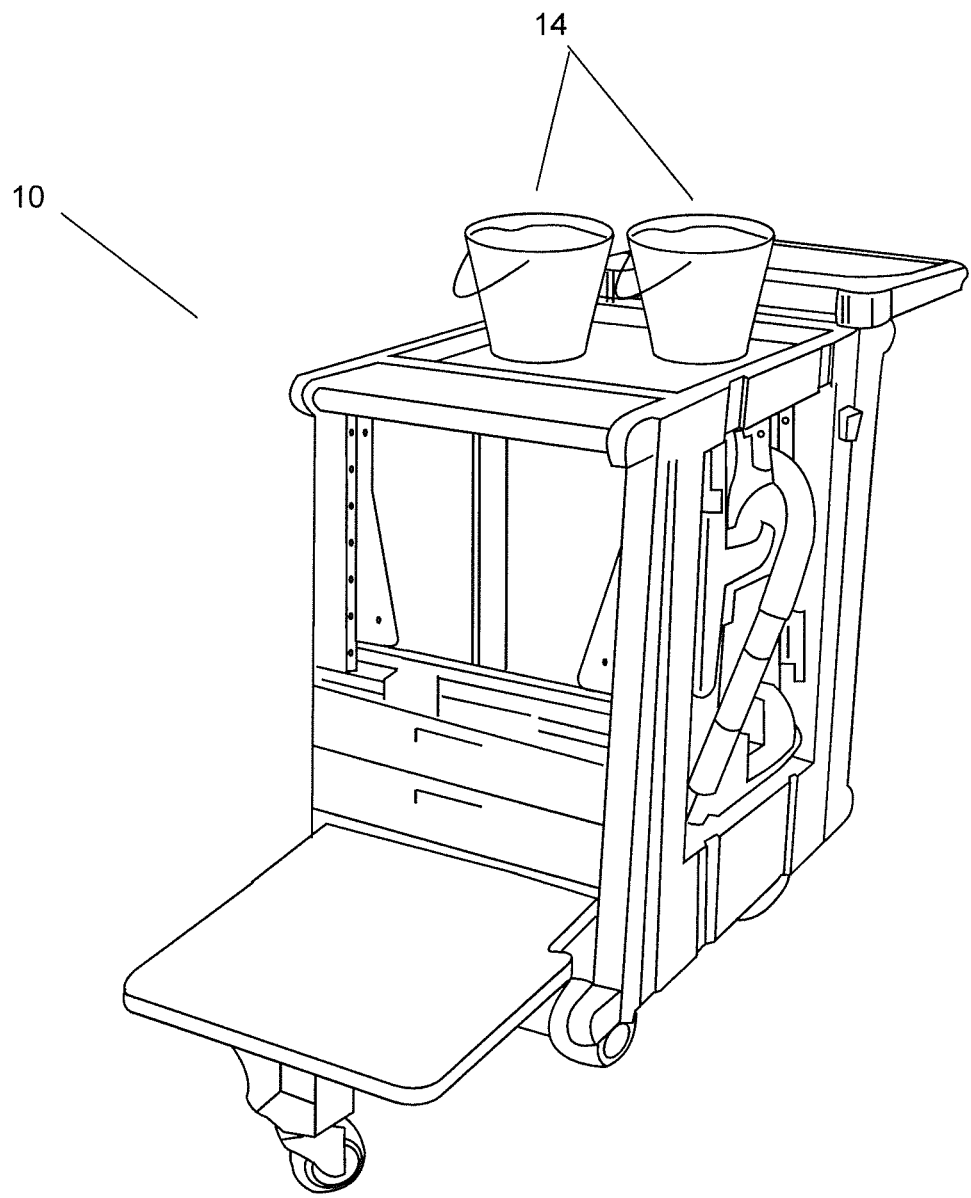
FIG. 2 is a front perspective view of a cleaning cart.

As shown in FIG. 1 and FIG. 2, the present invention is preferably implemented utilizing equipment such as a cleaning cart 10 with a vacuum cleaning apparatus 12, buckets 14 positioned on or within the cart 10, a plurality of single-use cloths 16, a plurality of single-use mops 18, and a mobile trash apparatus 20. As discussed in more detail below, the equipment including the cart 10 and the wheeled trash barrel is utilized by a plurality of team members to clean a patient area, including a patient room, bathroom, and floor area. However, the various embodiments of the present invention may be utilized to clean any area.

The cart 10 is preferably a Cartmaster Total Environment Cleaning System manufactured by M.D. Manufacturing, Inc. of Bakersfield, Calif. However, the vacuum cart 10 may comprise any mobile vacuum elements, preferably with HEPA filtering. For example, in some embodiments the vacuum cart 10 may comprise a conventional wheeled cart having a HEPA filtered vacuum positioned thereon. The vacuum cleaning cart 10 and cleaning cart 12 also preferably includes buckets 14 that contain cleaning solution in which to soak single-use cloths 16 and microfiber mops 18. The buckets 14 may be integrally formed within the cart 10 or be discrete elements that are removably transported on or within the cart 10. The cleaning solution could include a disinfectant such as bleach or a similar germicidal solution.

The single-use cloths 16 are preferably microfiber cleaning cloths available from Newell Rubbermaid Inc. in Atlanta, Ga., but may include any microfiber or lint-free wipes that have absorbency and strength when wet to allow for intense cleaning. The microfiber cloths are preferably launderable and reusable and can be hand or machine washed and dried at low temperature between 500 and 1000 times.

The single-use mops 18 are preferably made from Newell Rubbermaid Inc. in Atlanta, Ga., but may include any microfiber-type mops that are capable of being treated with a disinfectant. Microfiber mops not only are cheaper to utilize than traditional string mops because they require less water and cleaning or disinfecting solution, but they also offer better cleaning because they can get into crevices and along baseboards where traditional mops have trouble. Microfiber mops also offer the option of being launderable and reusable. One microfiber mop head can be used to mop the floor of one patient area and then discarded into a special bag or compartment in the cleaning cart. Another microfiber mop head can be installed on the mop handle to mop the next patient area. At the end of the shift, all the used mop heads can be washed in traditional laundry detergent and dried at low temperature for reusage during the next shift. The mop heads can be used repeatedly in this fashion between 100 and 500 times.

The mobile trash apparatus 20 is preferably a 32-gallon round container, Model #2632WH, mounted or coupled with a dolly, Model #2640, both manufactured by Newell Rubbermaid Inc. in Atlanta, Ga., but may include any container capable of holding trash that is mobile or can be adapted to a dolly or the like.

The mobile cleaning equipment has been described above as preferably including three discrete elements—the vacuum cart 10, the supply cart 12, and the mobile trash apparatus 20. However, in some embodiments, the carts 10, 12 and apparatus 20 may be combined into any combination of carts, including a single cart including vacuum, cleaning, and trash elements. For example, as shown in FIG. 2, the vacuum cart 10 may include the buckets 14 and other cleaning supplies such that use of the supply cart 12 is not required. In another alternative embodiment, the supply cart 12 may be equipped with both a vacuum apparatus and a trash receptacle.

Figure 4:
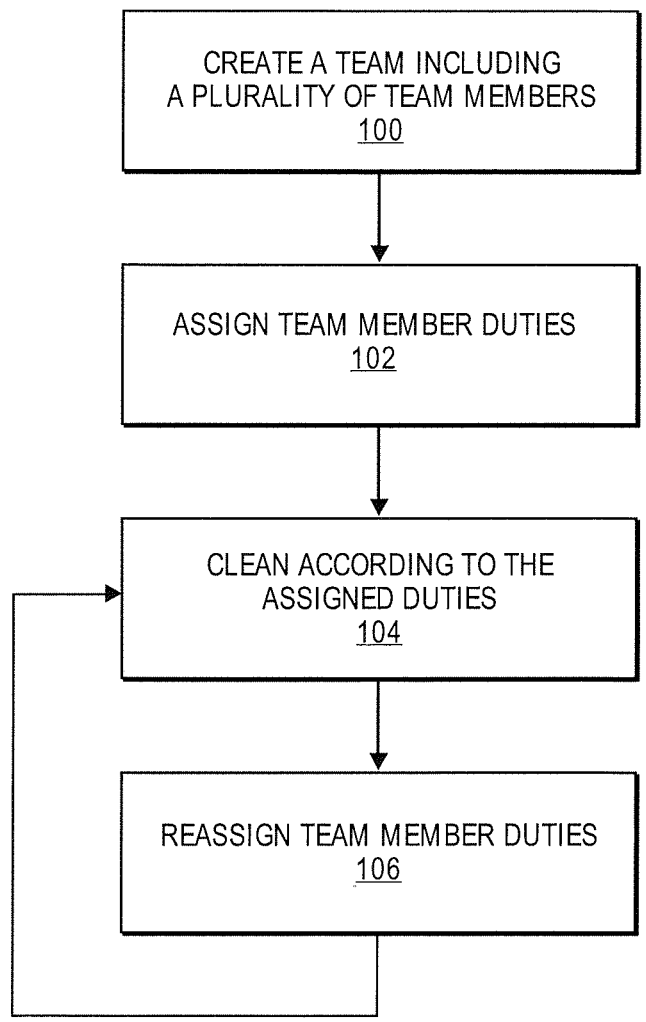
FIG. 4 is a flow chart showing some of the steps that may be performed by various embodiments of the present invention.

Steps 100-106 shown in FIG. 4 generally illustrate a method operable to be performed by various embodiments of the present invention. Steps 100-106 generally include: creating a plurality of team members, referenced at step 100; assigning team member duties, referenced at step 102; cleaning according to the assigned duties, referenced at step 104; and reassigning team member duties, referenced at step 106.

Figure 3:
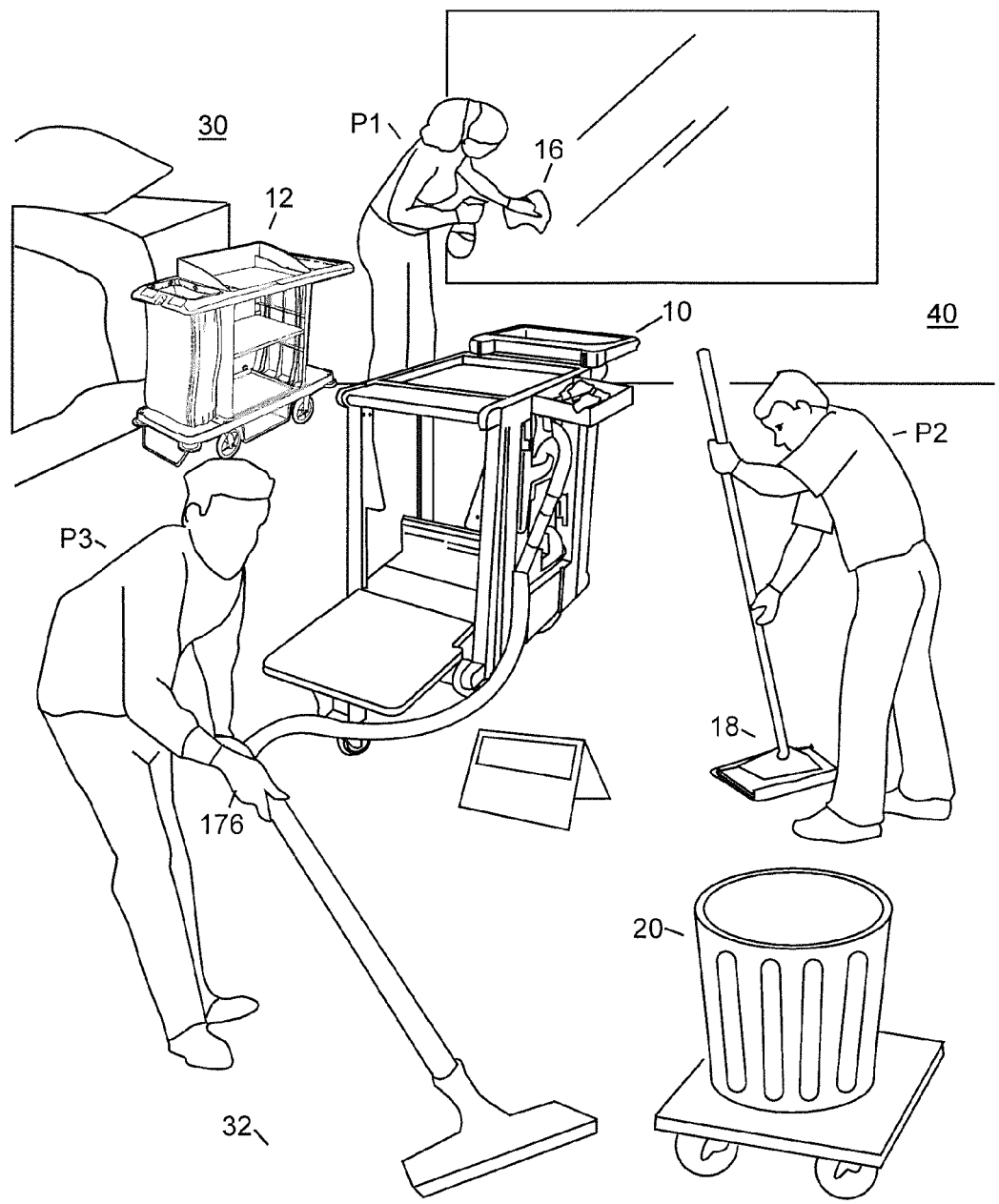
FIG. 3 is a perspective view of a cleaning team cleaning a patient area.

In step 100, a cleaning team is created with a plurality of members. The number of team members can vary from two to three, however, three team members is the preferred embodiment. Two team members will require more time to complete the tasks. Three team members are preferable because the tasks to be assigned can easily be divided into threes, allowing many of the tasks to be performed simultaneously. As a result, for a three-member team, the tasks are readily rotated and can be completed in an efficient and effective manner. As shown in FIG. 3, the various team members preferably include a first team member P1, a second team member P2, and a third team member P3.

In step 102, the individual team members are assigned specific tasks to perform. The first and second team members P1, P2 are assigned the task of moving through the patient area 40 to remove trash. Specifically, the first and second team members P1, P2 also are assigned the task of scanning all floor areas 32 for large debris that may block or interfere with the cart 10 and vacuum apparatus 12. The first and second team members P1, P2 preferably place removed trash and debris in the mobile trash apparatus 20 for easy transport and disposal. The third team member P3 is assigned the task of vacuuming the floor area utilizing the vacuum apparatus 12 after the debris are removed from the floor area. The first team member P1 is assigned the task of damp cleaning the patient area 40 with single-use cloths 16, which are preferably discarded after cleaning a single patient area into a separate bag, located in the cart 10, and laundered later. The first team member P1 also mops the floor area 32 with a microfiber mop 18, which is discarded after mopping the floor area of a single patient area into a separate bag, within the cart 10, and laundered later. The second team member P2 repeats the same set of tasks as team member P1, but in the next assigned patient area.

While the preferable assignments for step 102 are discussed above, other combinations and variations are possible. For example, first and third team members may be assigned the task of removing debris from the floor area, while the second team member is assigned to vacuum the floor. Other assignment combinations are also possible.

In step 104, the patient area 40 is cleaned according to the tasks assigned in step 102. For example, as shown in FIG. 3, the first team member P1 cleans the patient's room 30 of the patient area 40 with one or more disinfected cloths 16 obtained from the cart 10 and mops all floor areas 32 with the damp, microfiber mop 18. The second team member P2 repeats the same tasks as P1 in the next assigned patient area. The third team member P3 vacuums the floor area 32 with the vacuum cleaning apparatus 12. Any debris encountered can be disposed of in the mobile trash apparatus 20. In some embodiments, the second and third team members P2 and P3 may mop the floor area 32 utilizing any equipment and the first team member P1 may damp clean the patient area 40 with any equipment.

As should be appreciated, the team members P1, P2, P3 may clean the various areas without actually cleaning or accessing every portion of the areas. Thus, as utilized herein, "clean" means to clean at least a portion of an area. For instance, step 104 may be completed by vacuuming a portion of the floor area 32 with the vacuum cart 10, by picking up only a portion of encountered debris, by cleaning only a portion of areas and surfaces with the cloths 16 and mops 18, etc.

Step 104 is preferably repeated for each patient area. For instance, in hospital settings, a plurality of patient areas may exist each corresponding to a hospital room or other area. In such embodiments, each patient area is cleaned as discussed above. Cleaning a plurality of patient areas according to the various embodiments of the present invention increases cleanliness and reduces the risk of contamination. Specifically, as the cloths 16 and mops 18 are single-use, each cloth or mop is only utilized to clean a single patient area until it is laundered or otherwise sterilized. Such a configuration reduces the risk of contamination and increases cleanliness by preventing bacteria and other undesirable substances from being spread between patient areas. Further, the embodiments of the present invention enable many areas to be efficiently and effectively cleaned due to the team member assignments and use of the carts 10, 12 and trash apparatus 20.

In step 106, the team members rotate tasks after a given period of time in order to avoid boredom and fatigue. The preferable period of time is approximately thirty minutes. For instance, after about thirty minutes, the third team member P3 will perform the first team member's P1 tasks, the first team member P1 will perform the second team member's P2 tasks, and the second team member P2 will perform the third team member's P3 tasks. The rotation continues on the given schedule as long as the team is active. As should be appreciated, the tasks may be rotated after any interval to increase team member efficiency and productivity.

It is known that medical facility patient discharge volume increases about 11:00 am. All patient areas in which the patient will continue to stay should be cleaned by 11:30 am. At this time, the team members finish cleaning the patient area they currently working on. Once finished, they move to a patient area where the patient has recently been discharged and they clean the patient area, performing the steps discussed above. The team members continue cleaning the areas where patients have been discharged until all recently-discharged patient areas have been cleaned. There is no disruption to the workflow, but merely a priority given to those areas where patients have recently been discharged. As a result, beds are available sooner for the admission of a new patient.

Figure 14:
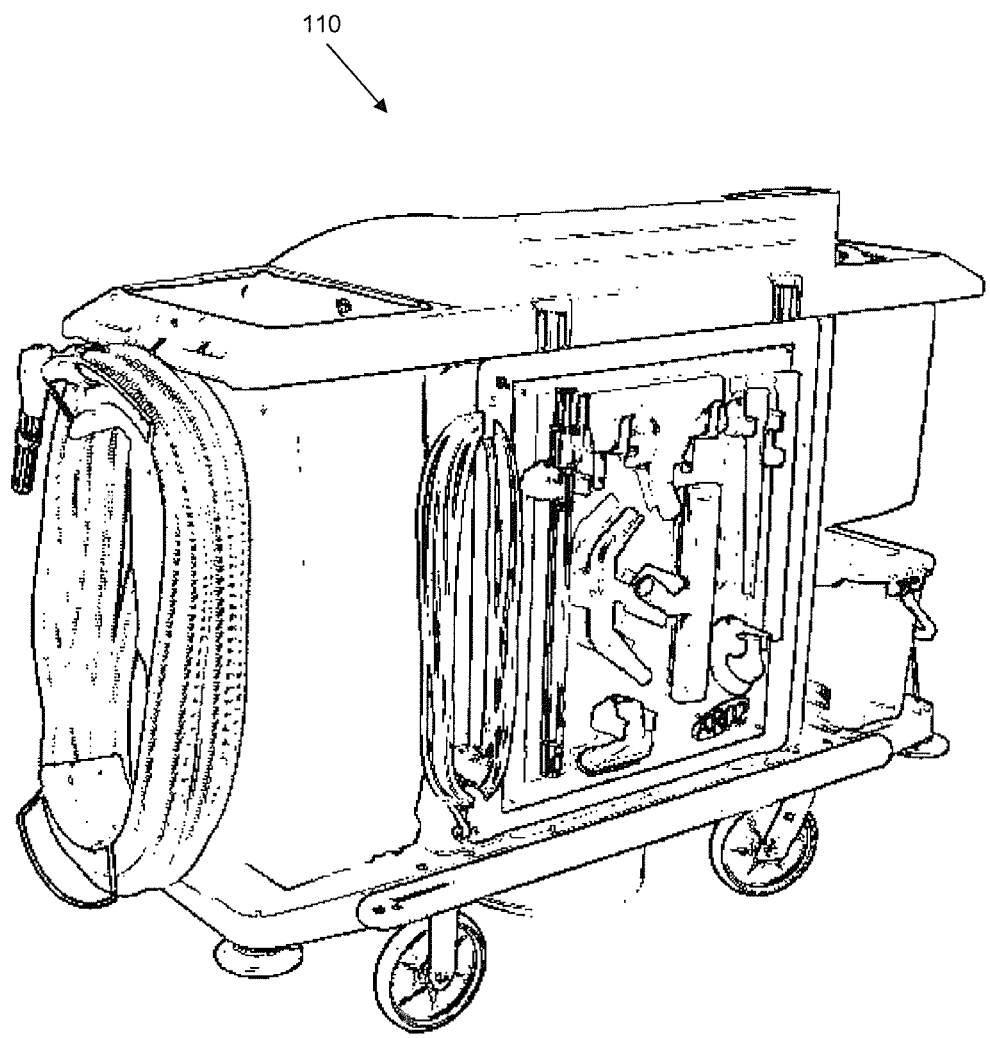
FIG. 14 is a perspective view of a third embodiment of the cleaning cart.
Figure 15:
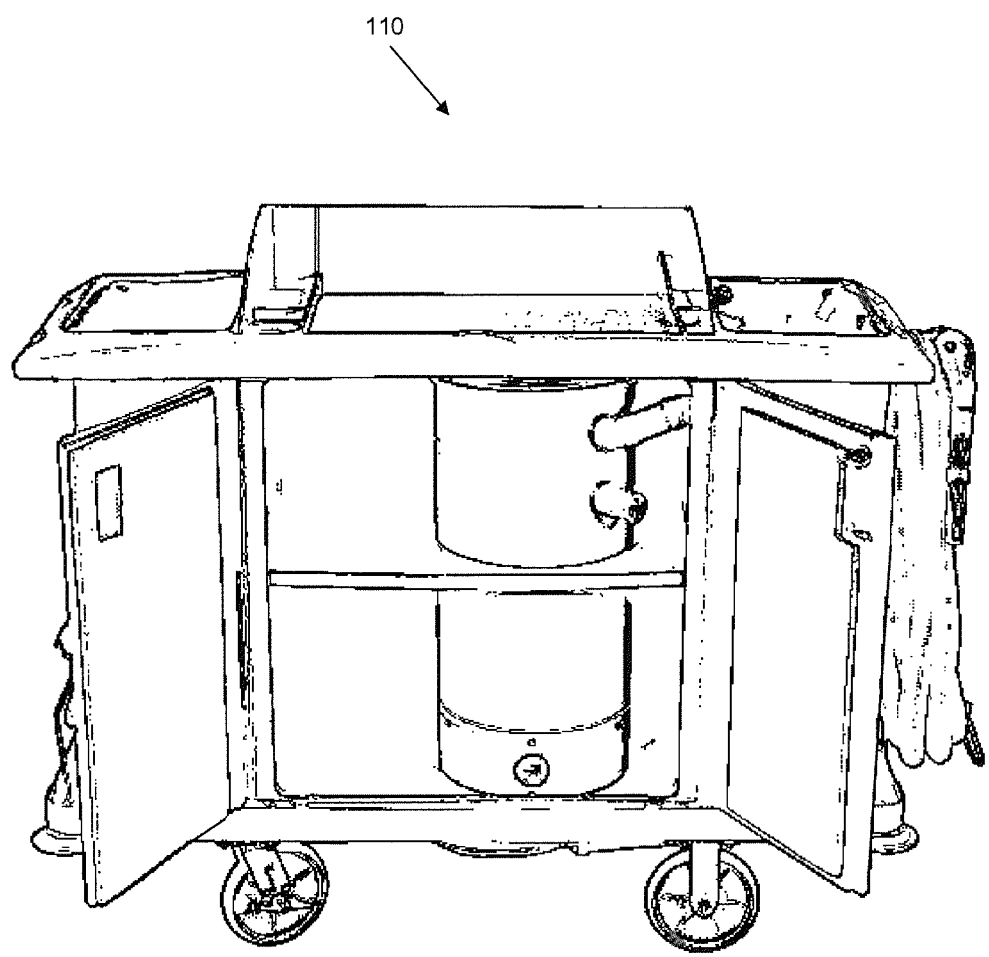
FIG. 15 is a perspective view of the third embodiment of the cleaning cart showing the interior thereof.

A second embodiment of the present invention includes a method 200 of improving air quality and reducing healthcare-associated infections in a patient area. The method may be performed by one or more team members P1, P2, P3. The method 200 may utilize the cleaning cart 100 of FIG. 5, or the cleaning cart 110 of FIGS. 14-15. The method 200 may further utilize the buckets 14, the single-use microfiber cloths 16, the single-use microfiber mops 18, and the mobile trash apparatus 20, described in connection with the first embodiment of the invention.

Figure 5:
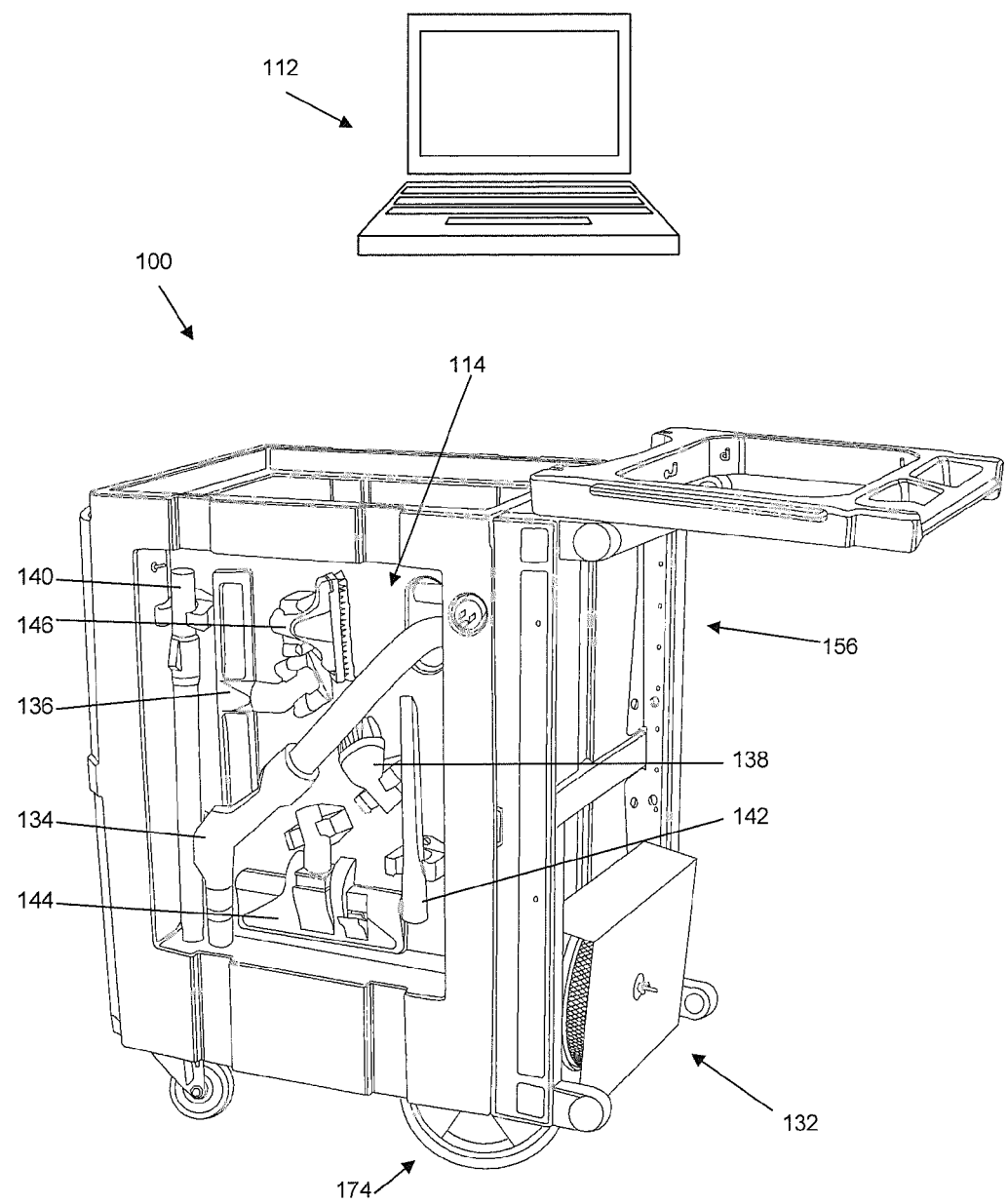
FIG. 5 is a perspective view of a second embodiment of the cleaning cart.

The method 200 may be developed, generated, or programmed using a computer 112, as seen in FIG. 5. The computer 112 may include a palmtop computer, a notebook computer, a laptop computer, a desktop computer, a workstation, a tablet computer, handheld electronic devices such as a cell phone or personal digital assistant, and the like. The computer 112 may include one or more of the following: a processor, a microprocessor, a microcontroller, a field programmable gate array (FPGA), and the like. The computer may also include memory elements that may be considered a "computer-readable storage medium", such as read-only memory (ROM), random-access memory (RAM), hard-disk drives. The computer 112 may also be able to read other computer-readable storage media, such as compact discs (CDs), digital video discs (DVDs), Blu-Ray™ discs, flash memory, and the like.

The cleaning cart 100, 110 may include a vacuum cleaning apparatus 114, a shell 116, a lid 118, a first frame member 120, a second frame member 122, a hose reel mechanism assembly 124, a rear axle 126, a plurality of brackets 128, and a hook 130. An exemplary cleaning cart 100, 110 may be the XRO1, XRO2, or XRO2.2, manufactured by M.D. Manufacturing, Inc. of Bakersfield, Calif.

The vacuum cleaning apparatus 114 may include components that create suction by which dust, debris, and small particles are removed from surfaces. The suction enables a high-level of removal of even the smallest particles of dust, dirt and particle removal that can be the source of certain nosocomial infections, such as Aspergillus. A vacuum cleaning apparatus 114 this powerful would normally generate too much heat to be enclosed within the cleaning cart 100, 110 structure. The vacuum cleaning apparatus 114 and the cleaning cart 100, 110 have been specially engineered to reduce heat emanation and avoid overheating of the cleaning cart 100, 110 and the vacuum cleaning apparatus 114.

The vacuum cleaning apparatus 114 may also include a filtration system 132 positioned at least partially on the shell 116 at the rear of the cleaning cart 100, 110. The filtration system 132 may include four stages. In some embodiments, the filtration system 132 is HEPA certified. In other embodiments, the filtration system 132 is ultra-low particulate air (ULPA) certified. The filtration system 132 may also capture dust that is generated from a motor (not shown) that generates the suction for the vacuum cleaning apparatus 114.

The vacuum cleaning apparatus 114 may further include a noise dampening system, such as the system disclosed in U.S. Pat. No. 6,804,857, issued Oct. 19, 2004, which is incorporated by reference in its entirety into the present application. The noise dampening system may operate by using suction to pull noise generated from a vacuum motor back into the motor. The noise dampening system may allow the vacuum cleaning apparatus 114 to operate while generating approximately 53 decibels of sound pressure level.

In addition, the vacuum cleaning apparatus 114 may include a vacuum hose 134, a first attachment 136, and a second attachment 138. The vacuum hose 134 may be extensible from the cleaning cart 100, 110, with a proximal end coupled to thereto and an opposing distal end, and may be up to 30 feet in length. The vacuum hose 134 may be manufactured from a strengthened, crushproof material and coated with a microbiostatic agent, such as the Microbe Shield®, manufactured by Aegis Environments of Midland, Mich. In various embodiments, the vacuum hose 134 may be colored orange or a similar bright color to increase the visibility of the vacuum hose 134 for the cleaning personnel or others to avoid tripping over the vacuum hose 134. The first attachment 136 may be suitable for vacuuming non-floor surfaces, such as the horizontal surfaces of tables, stands, equipment, televisions, monitors, light diffusers, vents, window sills, radiators, and other surfaces in a medical facility patient room that may collect dust. The first attachment 136 may include a dusting brush which may include an oval or round shape. The second attachment 138 may be suitable for vacuuming floor surfaces and may include a wide, flat opening for removing dust and debris. Both the first attachment 136 and the second attachment 138 may be removably attached to the distal end of the vacuum hose 134.

The vacuum cleaning apparatus 114 may include additional removable attachments, such as an extension tube 140, a crevice tool 142, a secondary floor tool 144, and a secondary dust brush 146, as are commonly known.

Figure 6:
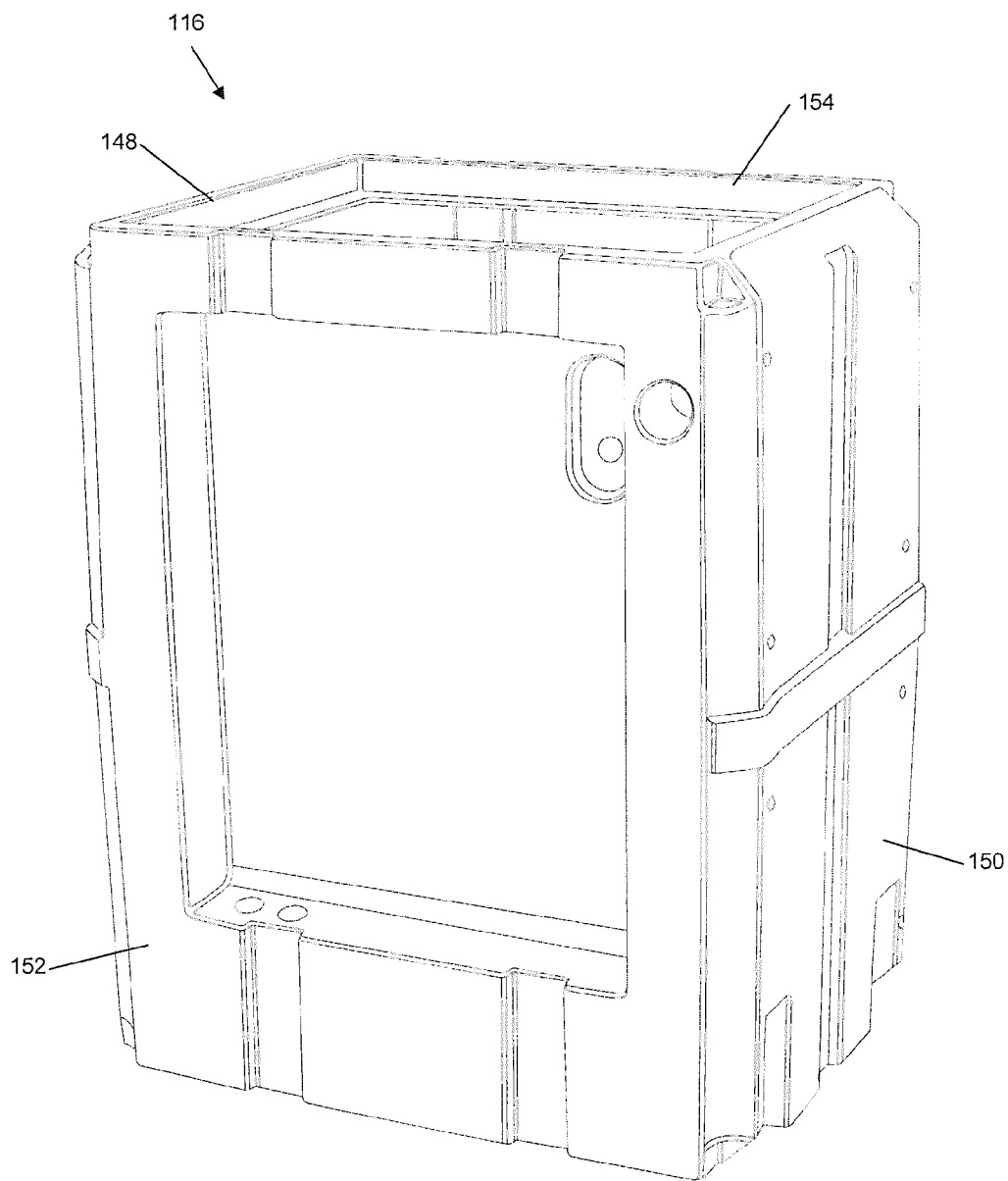
FIG. 6 is a perspective view of a shell of the cleaning cart.

The shell 116, shown in FIG. 6, may include front 148, back 150, left 152, and right 154 upright sidewalls. The sidewalls 148, 150, 152, 154 may be manufactured from hardened or strengthened plastic and may support or retain accessories for the vacuum cleaning apparatus 114 or general cleaning supplies. The shell 116 may couple with a frame 156 of the cleaning cart 100, 110. The shell 116 may further include sound insulation properties to further reduce noise generated by the vacuum cleaning apparatus 114.

Figure 7:
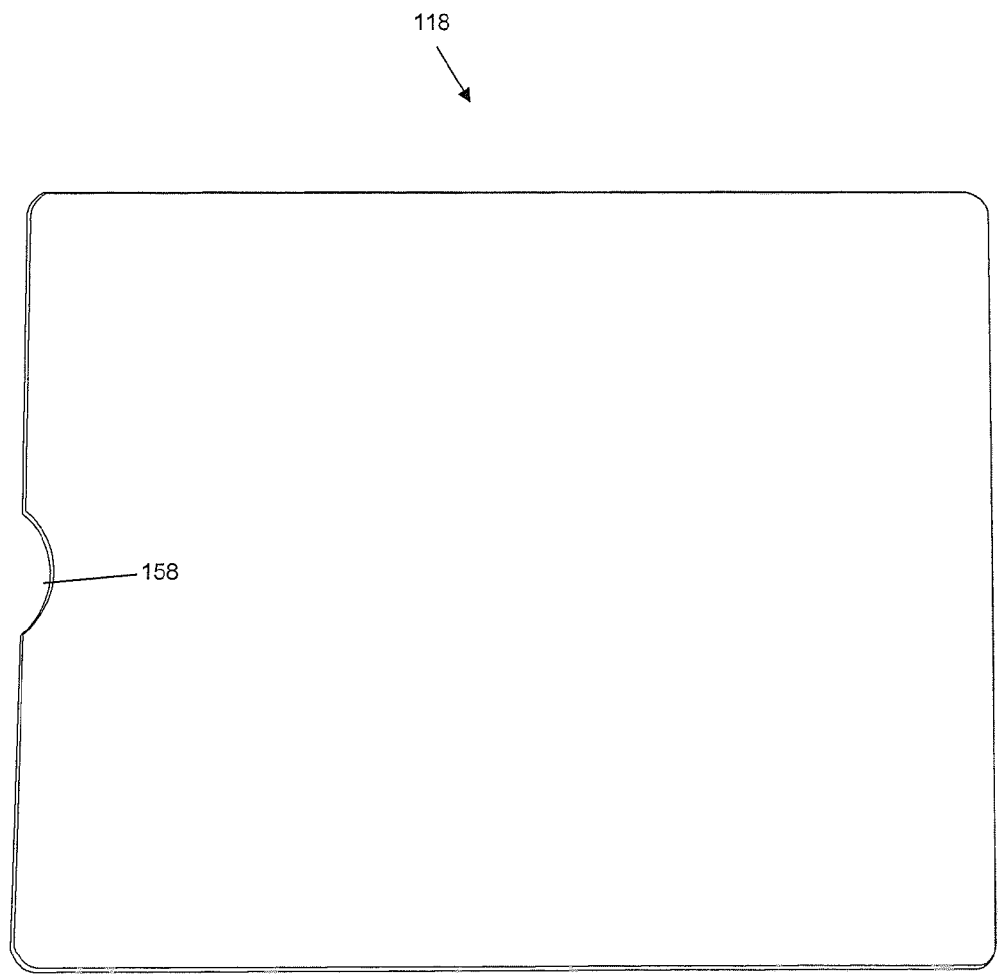
FIG. 7 is a top view of a lid of the cleaning cart.

The lid 118, shown in FIG. 7, may be generally planar and roughly rectangular in shape and may include an arcuate cutout 158 along one edge to facilitate opening or positioning of the lid 118. The lid 118 may be manufactured from plastic, such as PVC. The lid 118 may be positioned on top of the shell 116.

Figure 8:
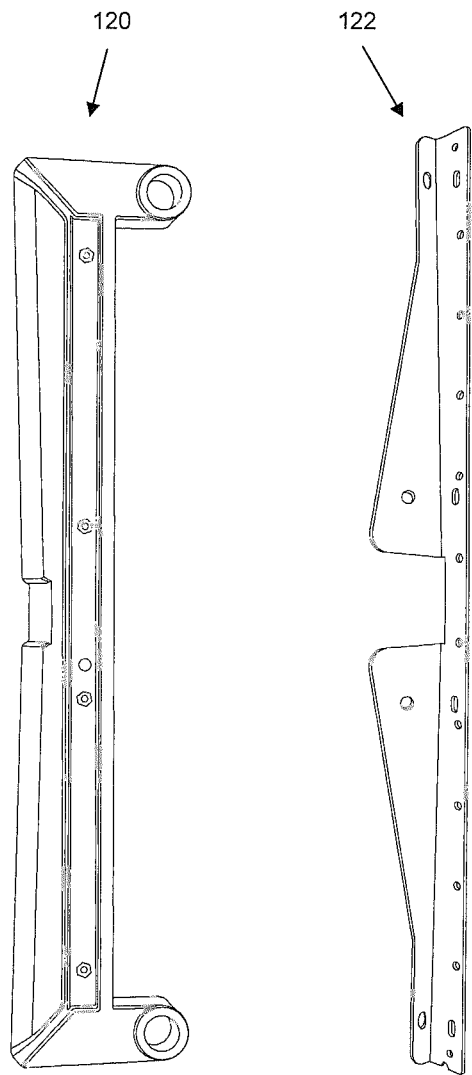
FIG. 8 is a top view of first and second frame members of the cleaning cart.

The first frame member 120 and the second frame member 122, shown in FIG. 8, may be generally elongated with various features such as cutouts, holes, flanged or flared portions, and the like. The first frame member 120 and the second frame member 122 may generally adapt or retain the shell 116 to the frame 156.

Figure 9:
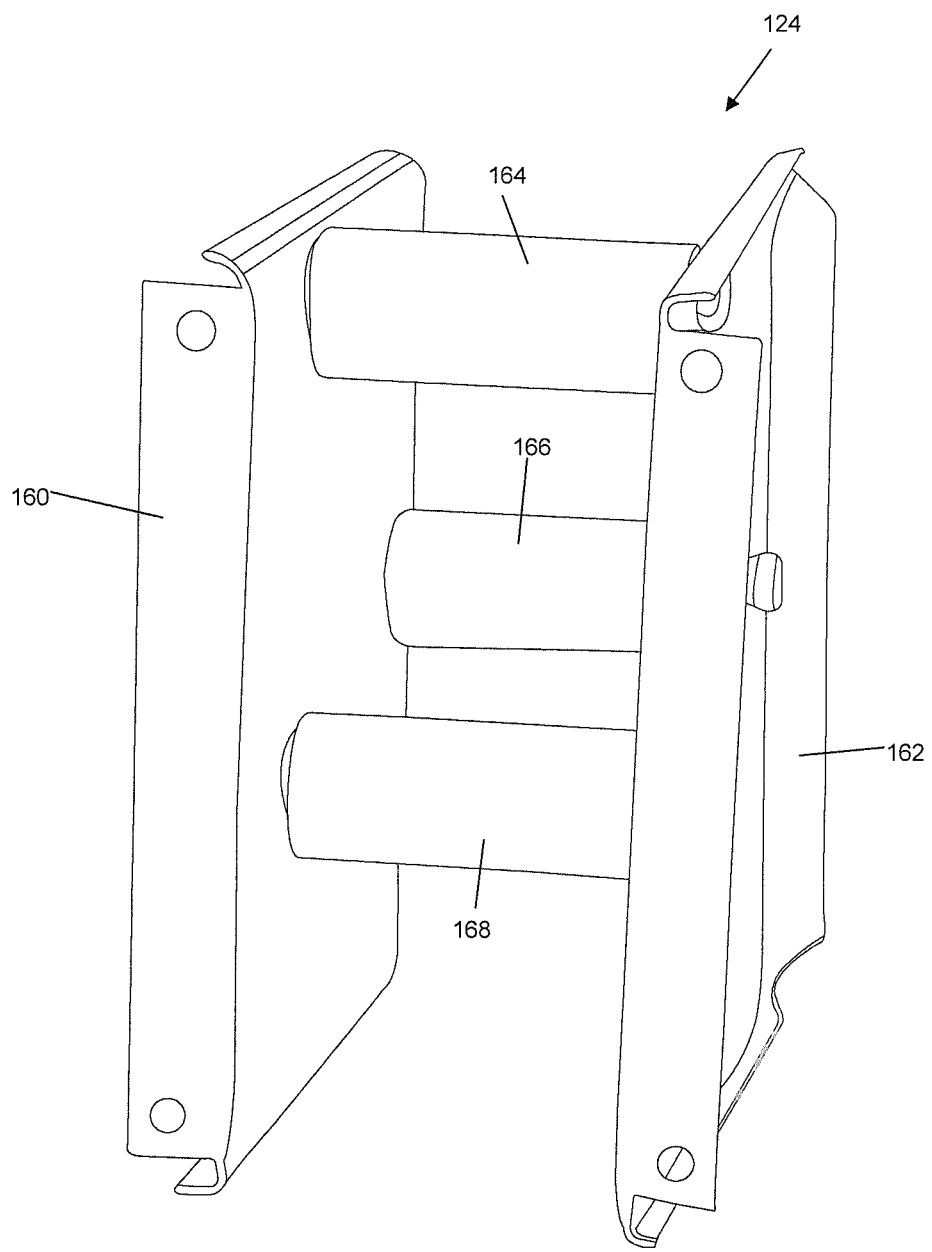
FIG. 9 is a perspective view of a hose reel mechanism assembly of the cleaning cart.

The hose reel mechanism assembly 124, shown in FIG. 9, may include first 160 and second 162 spaced-apart and opposing sidewalls, and first 164, second 166, and third 168 spools. The spools 164, 166, 168 may be positioned between the first and second sidewalls 160, 162 and may retain and/or automatically reel in the vacuum hose 134. The hose reel mechanism assembly 124 may be positioned within the shell 116.

Figure 10:
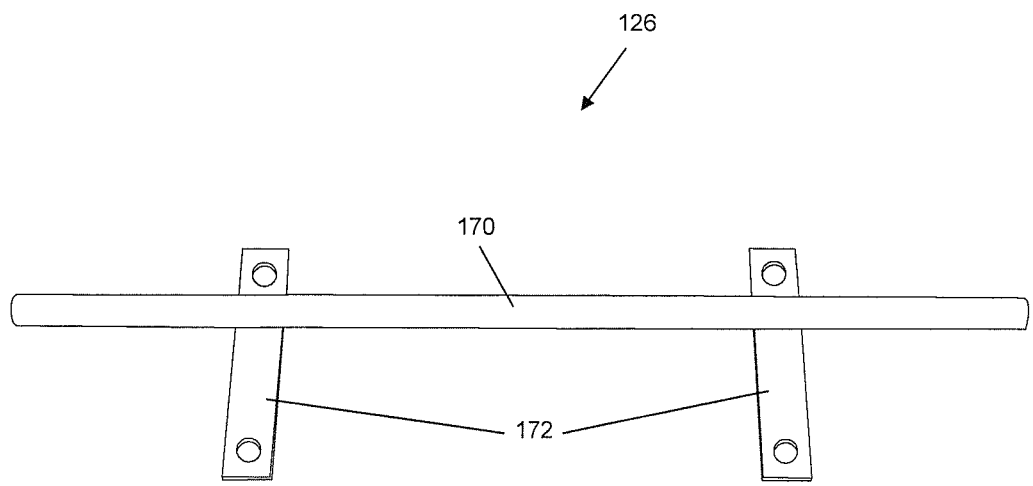
FIG. 10 is a perspective view of a rear axle of the cleaning cart.

The rear axle 126, shown in FIG. 10, may include an elongated rod 170 and a pair of mounting members 172. The rod 170 may be rigidly attached to the mounting members 172 and may be rotatably coupled with rear wheels 174 of the cleaning cart 100, 110. The mounting members 172 may be attached to the bottom of the shell 116, thereby holding the rear wheels 174 in a fixed orientation.

Figure 11:
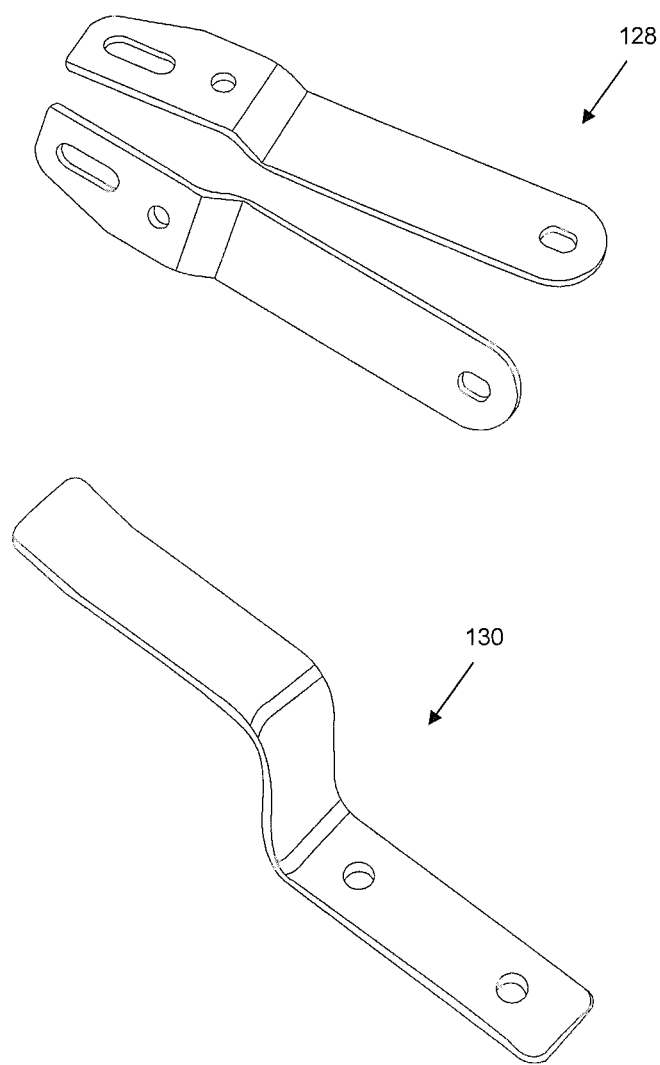
FIG. 11 is a perspective view of brackets and a hook of the cleaning cart.

The brackets 128, shown in FIG. 11, may be generally elongated with bends along the longitudinal axis to create an offset and may include a plurality of holes for mounting. The brackets 128 may be manufactured from metal and may be positioned on the shell 116 to hold linens or a trash receptacle.

The hook 130, shown in FIG. 11, is similar to the brackets 128 and may be generally elongated with bends along the longitudinal axis to create an offset and may include a plurality of holes for mounting. The hook 130 may be manufactured from metal and may be positioned on the shell 116 to hold a power cord or accessories.

Figure 12:
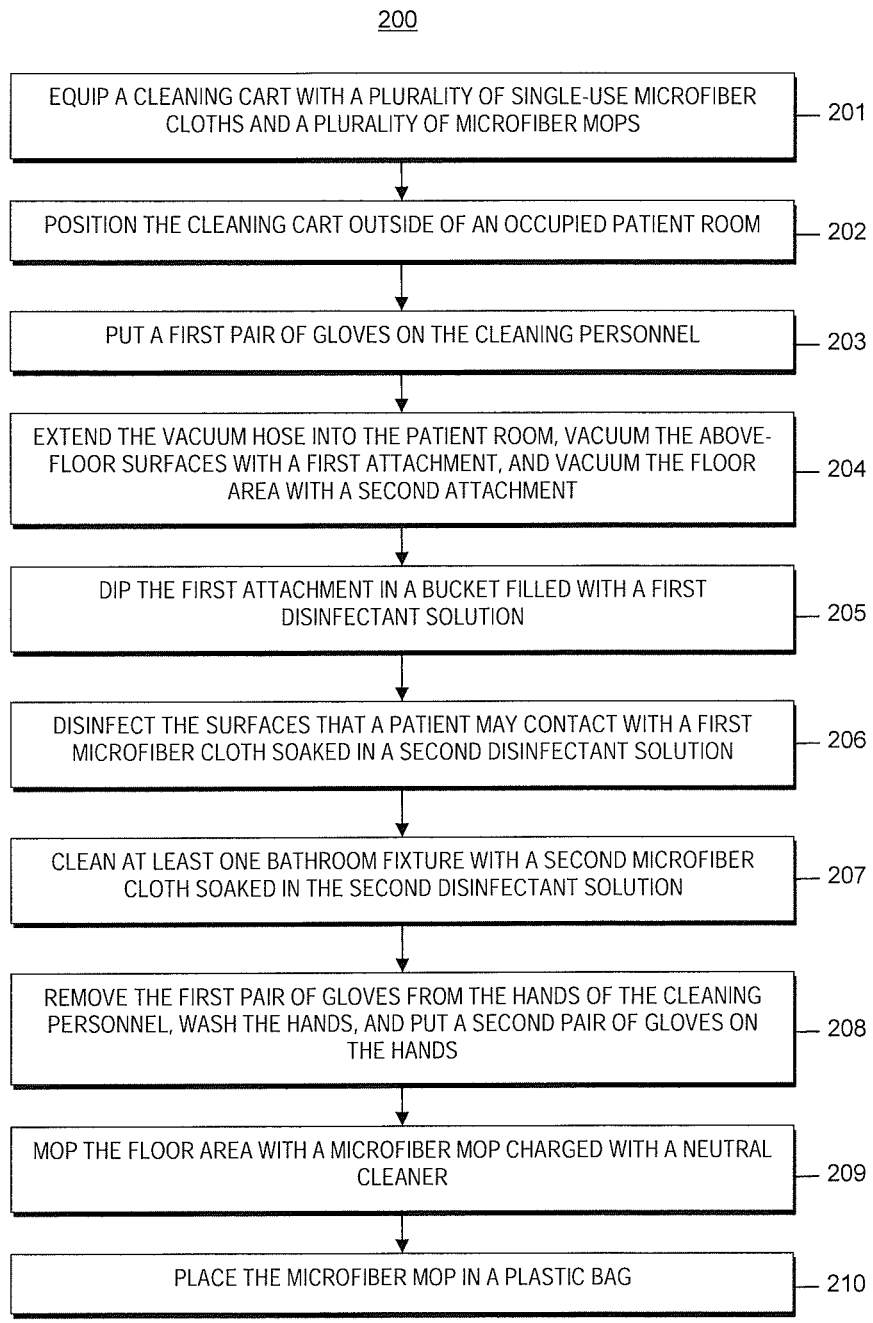
FIG. 12 is a listing of some of the steps of a method, constructed in accordance with one embodiment of the present invention, of improving air quality and reducing healthcare-associated infections performed by a cleaning personnel in a patient area.

At least a portion of the steps of the method 200 for improving air quality and reducing healthcare-associated infections performed by a cleaning personnel in a patient area including a patient room, a patient restroom, and a floor area, in accordance with various embodiments of the present invention, is shown in FIG. 12. The steps may be performed in the order as shown in FIG. 12, or they may be performed in a different order. Furthermore, some steps may be performed concurrently as opposed to sequentially. In addition, some steps may be optional or altered.

Referring to step 201, a cleaning cart 10 is equipped with a plurality of single-use microfiber cloths 16 and a plurality of microfiber mops 18. The cleaning cart 10 may include a vacuum cleaning apparatus 12 with an extensible vacuum hose 134 and a plurality of attachments. The vacuum hose 134 may be coated with a microbiostatic agent. The attachments may include a first attachment 136, such as a dust brush, and a second attachment 138, such as a floor tool.

Referring to step 202, the cleaning cart 10 is positioned outside of an occupied patient room. This helps to minimize the number of foreign objects that are brought into the patient room, thereby reducing the chance of cross contamination. This step also reduces the amount of noise that is generated inside the patient room.

Referring to step 203, the cleaning personnel puts on a first pair of gloves 176.

Referring to step 204, the vacuum hose 134 is extended into the patient room, the above-floor surfaces are vacuumed with a first attachment 136, and the floor area is vacuumed with a second attachment 138. The first attachment 136 may include a dust brush. The second attachment 138 may include a floor tool. The above-floor surfaces may include horizontal surfaces, such as vents, televisions, monitors, light diffusers, radiators, window sills, and the like. The above-floor surfaces may be vacuumed starting near the door to the hallway and continuing around the room systematically until returning to the door.

The floor surfaces may be vacuumed by first moving objects away from the walls and vacuuming along the baseboards in a straight-line motion. Objects may be moved from the rest of the floor. The rest of the floor may be vacuumed using back and forth sweeping motions while keeping the vacuum hose 134 behind the cleaning personnel.

Referring to step 205, the first attachment 136 is dipped in a bucket filled with a first disinfectant solution. The first attachment 136 may be dipped for a few seconds. Afterwards, the first attachment 136 may be allowed to air dry. The first disinfectant solution may include a germicide or bleach.

Referring to step 206, the surfaces that a patient may contact are disinfected with a first microfiber cloth 16 that is soaked in a second disinfectant solution. The surfaces may be generally wiped in order to disinfectant them. The second disinfectant solution may include a germicide.

Referring to step 207, at least one bathroom fixture is cleaned with a second microfiber cloth soaked in the second disinfectant solution. The bathroom fixtures may include faucets, dispensers, grab rails, shower stalls, and the like. The toilet may be wiped last before discarding the second cloth. A bowl mop and toilet cleaner may be used to clean the toilet bowl.

Referring to step 208, the cleaning personnel removes the first pair of gloves 176, washes his or her hands, and puts on a second pair of gloves 176.

Referring to step 209, the floor area is mopped with a microfiber mop 18 charged with a neutral cleaner. The floor area may be mopped starting at a far corner opposite the door to the hallway. The floor along the baseboards may be mopped in a straight line motion. The rest of the floor area may be mopped using a back and forth "S"-type motion. The floor area under furniture and other objects should be mopped as well. The floor area should be mopped in the direction of the door.

Referring to step 210, the microfiber mop 18 is placed in a plastic bag. Other items may be placed in the plastic bag as well. The plastic bag is generally retained with the cleaning cart 100, 110, and the contents of the plastic bag may be cleaned or discarded at the end of a work shift.

A third embodiment of the present invention includes a method 300 of improving air quality and reducing healthcare-associated infections in an isolated patient area. The method 300 may be performed by one or more team members P1, P2, P3. The method 300 may also utilize the same equipment as discussed above for the method 200.

Figure 13:
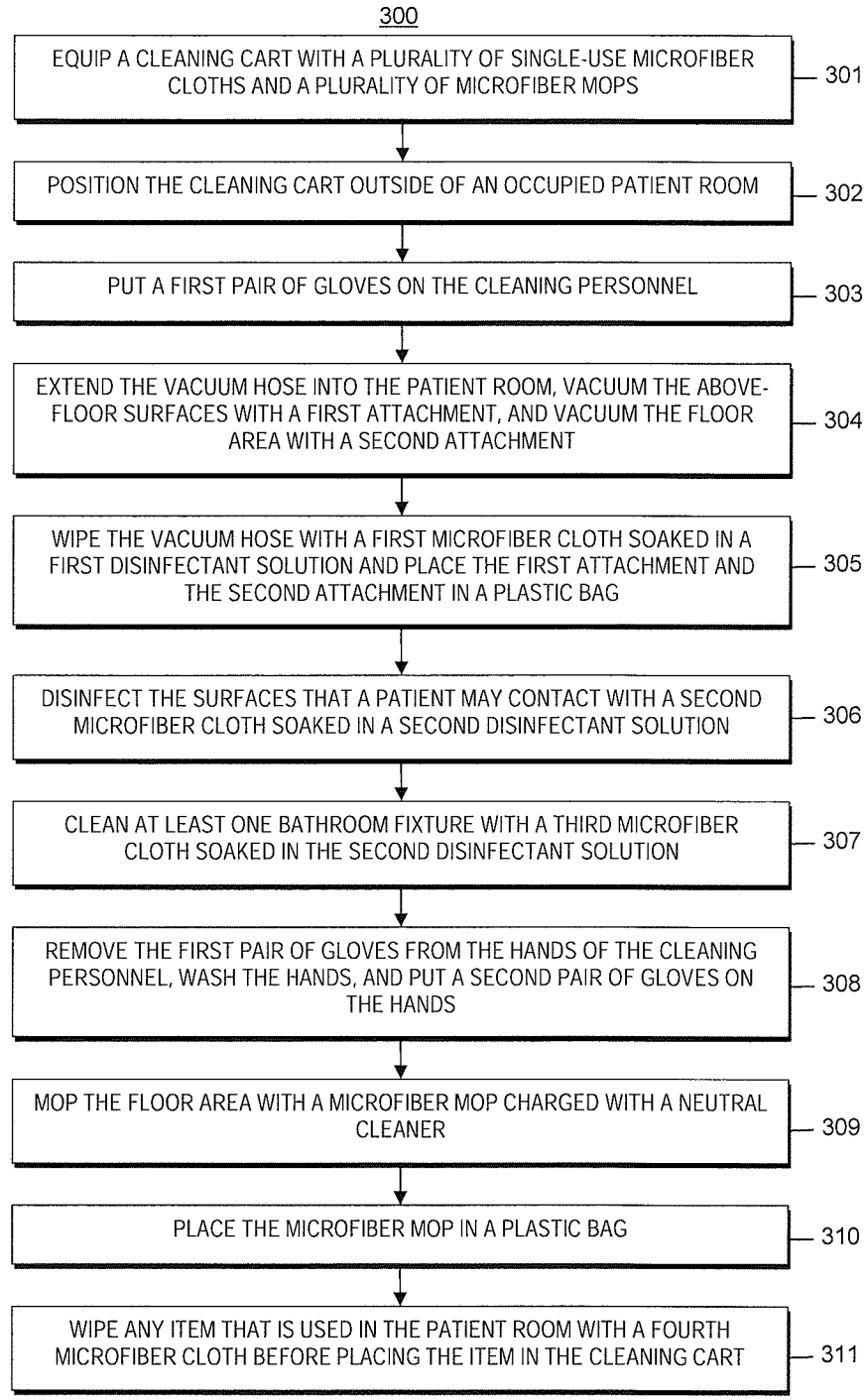
FIG. 13 is a listing of some of the steps of a method, constructed in accordance with another embodiment of the present invention, of improving air quality and reducing healthcare-associated infections performed by a cleaning personnel in an isolated patient area.

At least a portion of the steps of the method 300 for improving air quality and reducing healthcare-associated infections performed by a cleaning personnel in an isolated patient area including a patient room, a patient restroom, and a floor area is shown in FIG. 13. The steps may be performed in the order as shown in FIG. 13, or they may be performed in a different order. Furthermore, some steps may be performed concurrently as opposed to sequentially. In addition, some steps may be optional or altered.

Referring to step 301, a cleaning cart 10 is equipped with a plurality of single-use microfiber cloths 16 and a plurality of microfiber mops 18. The cleaning cart 10 may include a vacuum cleaning apparatus 12 with an extensible vacuum hose 134 and a plurality of attachments. The vacuum hose 134 may be coated with a microbiostatic agent. The attachments may include a first attachment 136, such as a dust brush, and a second attachment 138, such as a floor tool.

Referring to step 302, the cleaning cart 10 is positioned outside of an occupied patient room. This helps to minimize the number of foreign objects that are brought into the patient room, thereby reducing the chance of cross contamination. This step also reduces the amount of noise that is generated inside the patient room.

Referring to step 303, the cleaning personnel puts on a first pair of gloves 176.

Referring to step 304, the vacuum hose 134 is extended into the patient room, the above-floor surfaces are vacuumed with a first attachment 136, and the floor area is vacuumed with a second attachment 138. The first attachment 136 may include a dust brush. The second attachment 138 may include a floor tool. The above-floor surfaces may include horizontal surfaces, such as vents, televisions, monitors, light diffusers, radiators, window sills, and the like. The above-floor surfaces may be vacuumed starting near the door to the hallway and continuing around the room systematically until returning to the door.

The floor surfaces may be vacuumed by first moving objects away from the walls and vacuuming along the baseboards in a straight-line motion. Objects may be moved from the rest of the floor. The rest of the floor may be vacuumed using back and forth sweeping motions while keeping the vacuum hose 134 behind the cleaning personnel.

Referring to step 305, the vacuum hose 134 is wiped with a first microfiber cloth 16 soaked in a first disinfectant solution. The first attachment 136 and the second attachment 138 are placed in a plastic bag. The vacuum hose may be wiped while the cleaning personnel is standing near the door facing the cleaning cart 100, 110. The plastic bag may be placed inside the patient restroom. The first disinfectant solution may include a germicide or bleach.

Referring to step 306, the surfaces that a patient may contact are disinfected with a second microfiber cloth 16 that is soaked in a second disinfectant solution. The surfaces may be generally wiped in order to disinfectant them. The second disinfectant solution may include a germicide.

Referring to step 307, at least one bathroom fixture is cleaned with a third microfiber cloth soaked in the second disinfectant solution. The bathroom fixtures may include faucets, dispensers, grab rails, shower stalls, and the like. The toilet may be wiped last before discarding the second cloth. A bowl mop and toilet cleaner may be used to clean the toilet bowl.

Referring to step 308, the cleaning personnel removes the first pair of gloves 176, washes his or her hands, and puts on a second pair of gloves 176.

Referring to step 309, the floor area is mopped with a microfiber mop 18 charged with a neutral cleaner. The floor area may be mopped starting at a far corner opposite the door to the hallway. The floor along the baseboards may be mopped in a straight line motion. The rest of the floor area may be mopped using a back and forth "S"-type motion. The floor area under furniture and other objects should be mopped as well. The floor area should be mopped in the direction of the door.

Referring to step 310, the microfiber mop 18 is placed in a plastic bag. Other items may be placed in the plastic bag as well. The plastic bag is generally retained with the cleaning cart 100, 110, and the contents of the plastic bag may be cleaned or discarded at the end of a work shift.

Referring to step 311, any item that is used in the patient room is wiped with a fourth microfiber cloth 16 before placing the item in the cleaning cart 100, 110. The items may include bottles of disinfectant or cleaning solution, portable caddies, and the like.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. A method of improving air quality and reducing the risk of healthcare-associated infections performed by three cleaning team members in a patient area including a patient room, a patient restroom, and a floor area, the method comprising:
   (a) positioning a cleaning cart outside of the patient room, the cleaning cart having a vacuum cleaning apparatus integrated therein equipped with a filter having at least an ULPA rating and an extensible vacuum hose attached thereto to clean the patient area, said hose being coated with a microbiostatic agent;
   (b) a first cleaning team member extending the vacuum hose from the cleaning cart into the patient room, wherein the cleaning cart remains positioned outside the patient area; and
   (c) vacuuming the above-floor surfaces with a first attachment including vacuuming all horizontal surfaces that are above shoulder height of the first team member before or after vacuuming the floor area with a second attachment, the vacuuming of the floor beginning at a door to the patient room and continuing systematically around the patient room until returning to the door;
   and second and third cleaning team members performing the steps of:
   (d) disinfecting the surfaces that a patient may contact with a first microfiber cloth soaked in a disinfectant solution;
   (e) cleaning at least one bathroom fixture with a second microfiber cloth soaked in the disinfectant solution; and
   (f) mopping the floor area including the floor area of the patient restroom with a microfiber mop charged with a neutral cleaner.

2. The method of claim 1, wherein step (c) further includes vacuuming radiators and window sills.

3. The method of claim 1, wherein step (c) further includes moving objects away from the walls, vacuuming along at least one baseboard in a straight motion, and vacuuming the entire floor using sweeping motions while maintaining the vacuum hose behind the first team member.

4. The method of claim 1, wherein step (f) further includes mopping beginning at a far corner opposite a door of the patient room, mopping in a straight line along at least one baseboard, and mopping the floor area in a back and forth motion from the far corner toward the door.

5. The method of claim 1, wherein the first attachment includes a dust brush.

6. The method of claim 1, wherein the second attachment includes a floor tool.

7. The method of claim 1, wherein the vacuum hose is crushproof.

8. The method of claim 1, wherein the vacuum cleaning apparatus includes noise dampening system that uses suction to pull noise generated from a vacuum motor back into the motor.

9. The method of claim 1, wherein the cleaning cart further includes a body with sound insulation.

\* \* \* \* \*